United States Patent
Li et al.

(10) Patent No.: US 9,238,632 B2
(45) Date of Patent: Jan. 19, 2016

(54) 3-CYANOANILINOALKYLARYLPIPERAZINE DERIVATIVE AND USE THEREOF IN PREPARING DRUGS

(71) Applicants: NHWA Pharma. Corporation, Jiangsu (CN); Shanghai Institute of Pharmaceutical Industry, Shanghai (CN)

(72) Inventors: Jianqi Li, Shanghai (CN); Guan Wang, Shanghai (CN); Guisen Zhang, Jiangsu (CN); Yali Li, Shanghai (CN); Xiangqing Xu, Jiangsu (CN); Xiaowen Chen, Shanghai (CN); Shicheng Liu, Jiangsu (CN); Song Zhao, Jiangsu (CN); Minquan Yu, Jiangsu (CN)

(73) Assignees: NHWA Pharma, Corporation, Jiangsu (CN); Shanghai Institute of Pharmaceutical Industry, Shanghai (CN)

( * ) Notice: Subject to any disclaimer, the term of this patent is extended or adjusted under 35 U.S.C. 154(b) by 0 days.

(21) Appl. No.: 14/391,658

(22) PCT Filed: Apr. 9, 2013

(86) PCT No.: PCT/CN2013/073940
§ 371 (c)(1),
(2) Date: Oct. 9, 2014

(87) PCT Pub. No.: WO2013/152712
PCT Pub. Date: Oct. 17, 2013

(65) Prior Publication Data
US 2015/0105399 A1  Apr. 16, 2015

(30) Foreign Application Priority Data
Apr. 9, 2012 (CN) .......................... 2012 1 0101908

(51) Int. Cl.
| | | |
|---|---|---|
| C07D 295/13 | (2006.01) |
| C07D 239/47 | (2006.01) |
| A61K 31/495 | (2006.01) |
| C07D 239/34 | (2006.01) |
| C07D 295/125 | (2006.01) |

(52) U.S. Cl.
CPC ............ *C07D 295/13* (2013.01); *A61K 31/495* (2013.01); *C07D 239/34* (2013.01); *C07D 239/47* (2013.01); *C07D 295/125* (2013.01)

(58) Field of Classification Search
None
See application file for complete search history.

(56) References Cited

U.S. PATENT DOCUMENTS

| | | | |
|---|---|---|---|
| 5,532,242 A | 7/1996 | Cliffe | |
| 6,399,614 B1 * | 6/2002 | Leonardi et al. | 514/252.14 |
| 2004/0029887 A1 | 2/2004 | Bhatia et al. | |

FOREIGN PATENT DOCUMENTS

NL  WO2006/061378  *  6/2006  ........... A61K 31/423

* cited by examiner

*Primary Examiner* — Dennis Heyer
(74) *Attorney, Agent, or Firm* — Stoel Rives LLP

(57) ABSTRACT

Disclosed in the present invention is a 3-cyanoanilinoalkylarylpiperazine derivatives and use thereof in preparing drugs; the 3-cyanoanilinoalkylarylpiperazine derivatives disclosed by the present invention has very useful pharmaceutical properties and good tolerance, especially the use as novel analgesic drugs, novel antidepressants, and novel analgesic and antidepressive drugs. This class of compounds are central analgesics regulating 5-hydroxytrptamine, and also are novel antidepressants regulating 5-hydroxytrptamine. This class of compounds also has less toxic and side effects and a higher safety range. The 3-cyanoanilinoalkylarylpiperazine derivative is a compound shown as formula (III) or free base or salt thereof:

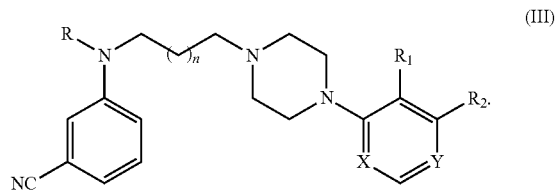

(III)

19 Claims, 1 Drawing Sheet ns.) 1975, 1: 511-521; Hynes el al., (Pharmacol. Toxicol.) 1999, 85:263-268; Sawynok el al., (Pain) 2000, 85: 311-312; (Expert Opinion on Drug Discovery), 2007, 2: 169-184 and so forth.
3-CYANOANILINOALKYLARYLPIPERAZINE DERIVATIVE AND USE THEREOF IN PREPARING DRUGS

CROSS-REFERENCE TO RELATED APPLICATIONS

This application is a national stage application under 35 U.S.C. §371 of International Application No. PCT/CN2013/073940, titled 3-CYANOANILINOALKYLARYLPIPERAZINE DERIVATIVE AND USE THEREOF IN PREPARING DRUGS, filed Apr. 9, 2013, which claims priority to Chinese Application No. 201210101908.2, filed Apr. 9, 2012, all of which are hereby incorporated by reference in their entireties.

TECHNICAL FIELD

The present invention relates to a 3-cyanoanilinoalkylarylpiperazine derivative and use in preparing an analgesic and antidepressant.

BACKGROUND ART

Severe acute and chronic pains mean that various destructive stimuli cause excitation of nociceptor, which is passed by the impulse of nociceptive information transmitting messenger to the central nerve system to cause nociception and algesia. Severe acute and chronic pains include tumor pains, postoperative pains, a variety of recurrent acute and chronic pains and the like. They had been troubled tens of millions of patients and are one big clinical problem currently.

Currently, analgesics broadly used in clinic are generally divided into the following three types: 1) non-steroid-anti-inflammatory analgesics 2) opioid analgesics 3) other non-opioid analgesics, including local anesthetics, antidepressants, antiepileptics and the like.

In case of clinical therapy, opioid analgesics are mainly used, or some non-steroid-anti-inflammatory analgesics are assisted for acute pains and tumor pains. Non-steroid-anti-inflammatory analgesics are seldom used alone for the above pains due to their poor analgesic effect, whereas the side effects of the opioid analgesics such as addiction, respiratory depression and gastric peristalsis decrease, limit their wide use. On the other hand, in the treatment of various chronic non-tumor pains and neuropathic pains, especially pathologic chronic pains, the therapeutic effects of opioid analgesics or non-steroid-anti-inflammatory analgesics are hardly satisfactory. In recent years, in the process of clinical application, some drugs for treating depression, epilepsy and anesthetic drugs are found to have excellent therapeutic effect to alleviate above pains.

Therefore, it is both the main research goal in analgesic field and the heat in innovative medicine research field to find wide spectrum analgesics which maintain strong analgesic effect as well as overcome numerous side effects of opioid analgesics and non-steroid-anti-inflammatory analgesics, to be safely used in clinic. In recent years, some big pharmaceutical companies abroad such as Pfizer, Merck of America etc. invest heavily to develop novel non-opioid analgesics.

Current non-opioid analgesics divided by mechanism mainly include: NMDA receptor antagonists (such as Ketamine), serotonin reuptake inhibitors (such as Tramadol), potassium ion channel openers (such as Flupirtine), cyclooxygenase-2 inhibitors (such as Celebrex), calcium ion channel antagonists (such as Ziconotide) and the like. Although these drugs have improvement in addiction and side effects over previous drugs, as reported in detail in, such as, U.S. Pat. No. 6,339,105, U.S. Pat. No. 4,481,205, U.S. Pat. No. 5,760,068, U.S. Pat. No. 5,189,020, but still have certain levels of addiction or high toxic and side effects. For example, Ketamine, Tramadol and Flupirtine still have addiction; Celebrex has latent cardiovascular side effects; Ziconotide can easily cause postural hypotension and the like. Meanwhile, the existing drugs are far from enough to meet the demand of various clinical patients for the pain control, especially for some tumor pains, severe chronic pains and some nerve pains, there are not any proper and safe analgesics at present. Therefore, there is need to develop novel structural non-addictive analgesics with less toxic and side effects and wide therapeutic ranges which are safe in clinical use so as to meet the demand of various patients suffering from pains. Meanwhile, non-opioid analgesics have growing massive market, and large social benefits and economic benefits will be generated if novel analgesics come out.

Selective serotonin reuptake inhibitors (SSRIs) have been confirmed to be effective in various animal and human pain indication tests. It has been demonstrated by lots of investigations that SSRIs not only can strengthen the effect of traditional opioid analgesic, but also have evident analgesic effect over acute pains, inflammatory pains and neuropathic pains in various animal models. For example, (Psychopharmacol. Commun.) 1975, 1: 511-521; Hynes el al., (Pharmacol. Toxicol.) 1999, 85:263-268; Sawynok el al., (Pain) 2000, 85: 311-312; (Expert Opinion on Drug Discovery), 2007, 2: 169-184 and so forth.

Selective 5-$HT_{1A}$ receptor agonists have been confirmed to effectively alleviate pains in animal acute and chronic pain models and inflammatory pain models. For example, (Meth. Find. Exp. Clin. Pharmacol.) 1999, 21: 161-165; Shannon and Lutz (Psychopharmacology) 2000, 149: 93-97; (Eur. J. Pharmacol.) 2004, 497, 285-292 and so forth.

Using selective serotonin reuptake inhibitors in combination with selective 5-$HT_{1A}$ receptor agonists rather than using selective serotonin reuptake inhibitors (SSRIs) alone, have better effect in treatment of chronic pain diseases, or in treatment of other diseases which are allergic to pain signal or algesia, with abnormal pain, enhancing pain sensation, enhancing pain memory and involve hypersensitisation effect. Above conclusion is further confirmed by related investigations, for example, (Prog. Neurobiol.) 2002, 66: 355-474; (Brain Res.) 2004, 1008, 288-292 and so forth.

Endogenous 5-HT generates various pain sensations by acting on 5-$HT_{2A}$ and 5-$HT_{2C}$ receptors of nervous tissue. By employing 5-$HT_{2A}$ antagonists or inverse agonists, various pains, especially acute inflammatory pains and pain allergies caused by various reasons, could be effectively supressed. (*Neurochem Int*, 2005, 47(6): 394-400. *Neuroscience*, 2005, 130(2): 465-474. *Pain*, 2006, 122(1-2): 130-136. *Eur J Pain*, 2008, In Press, Corrected Proof, Available online 24 July)

It is demonstrated by experiments, Trazodone possessing both 5-HT reuptake inhibitory effect and 5-$HT_{2A}$ antagonistic effect, has definite therapeutic effect towards continuous painful somatoform disorders, the clinical effect of which is better than that of ibuprofen. Combination of 5-HT reuptake inhibitor paroxetine with 5-$HT_{2A}$ antagonist ketanserine could clearly enhance the analgesic effect of the former in animal models (*J Pharmacol Sciences*, 2005, 97(1): 61-66).

Therefore, novel structural non-opioid analgesics possessing strong inhibitory effect to serotonin reuptake and affinity to 5-$HT_{1A}$ and 5-$HT_{2A}$ receptors, can not only have synergistic pharmaceutical effect to strengthen anti-neuropathic pain activities, but also have lower toxic and side effects. They are important research directions for development of novel anti-neuropathic pain drugs recently, regarding which inventive research is innovative and of important science value.

Serotonin reuptake inhibitors as antidepressants have been widely used in clinic, existing drugs mainly include: (1) selective serotonin reuptake inhibitor (SSRIs), such as Fluoxetine, Paroxetine; (2) specific serotonin reuptake and noradrenergic reuptake inhibitors (NDRIs), such as Mirtazapine; (3) serotonin and noradrenaline dual reuptake inhibitors (SNRIs), such as Venlafaxine and Duloxetine and so forth.

Investigation of antidepressants possessing dual effect of selective serotonin reuptake inhibitor and 5-$HT_{1A}$ receptor agonist is an important direction in this research field recently. Agonistic effect to 5-$HT_{1A}$ receptor can enhance anti-depression activities of serotonin reuptake inhibitors, and combination of the two has found clinical use. A medication of Vilazodone Hydrochloride, possessing the above-described dual target effect, had been approved by FDA to enter into the market in 2011 for treatment of adult depressions, with characteristics of high anti-depression efficiency and rapid onset of action etc. (J Clin Psychiatry. 2009, 70 (3):326-33). Acting on 5-$HT_{2A}$ receptor antagonist can also enhance anti-depression activity by adjusting serotonin levels in nerve synaptic cleft. For example, nefazodone, which possesses serotonin reuptake inhibitory effect and 5-$HT_{2A}$ receptor antagonistic effect, has been confirmed to have clear antidepression effects.

Therefore, novel antidepressants, which have multiple effects of strong inhibitory effect to serotonin reuptake and affinity to 5-$HT_{1A}$ and 5-$HT_{2A}$ receptors, can not only have strong anti-depression activities, but also have rapid onset of action and lower toxic and side effects etc. They are popular research directions for conducting and developing novel antidepressants recently, regarding which inventive research is innovative and of important science value.

DISCLOSURE OF THE INVENTION

One purpose of the present invention is to disclose a 3-cyanoanilinoalkylarylpiperazine derivative designed to overcome defects including addiction, respiratory depression, gastric peristalsis decrease and the like, and hence to address clinical problem and meet the demand for analgesia especially for anti-chronic neuropathic pains.

A second purpose of the present invention is to disclose the use of above-described compound as a novel antidepressant designed to overcome defects of existing antidepressants including high toxic and side effects, slow onset of action and the like, to expand the application choices of clinical antidepressants, and hence to meet the demand of depressed patients for drug treatment.

The 3-cyanoanilinoalkylarylpiperazine derivative of the present invention is a compound shown as formula (III) or its free base or salt thereof, wherein the salt is hydrochloride, hydrobromide, sulfate, tri-fluoroacetate or methanesulfonate, preferably is hydrochloride, hydrobromide, in which 0.5-3 molecules of crystal water may be contained.

(III)

wherein:
R represents $C_1$-$C_5$ linear or branched alkyl, wherein the hydrogen atom(s) of the alkyl may be optionally replaced by 1-3 fluorine atoms;
$R_1$ represents H, $OCH_3$, Cl or $CH_3$;
$R_2$ represents H, $CF_3$, Cl or $CH_3$;
X and Y independently represent CH or N;
n=0, 1 or 2;
preferably, R represents methyl, ethyl, trifluoromethyl, n-propyl or isopropyl;
preferably, R represents methyl, ethyl, trifluoromethyl, n-propyl or isopropyl; $R_1$ represents H, $OCH_3$, Cl or $CH_3$; $R_2$ represents H, $CF_3$, Cl or $CH_3$; X and Y independently represent CH or N; n=0 or 1;
preferably, when n=0, R represents methyl, ethyl, trifluoromethyl, n-propyl or isopropyl; $R_1$ represents H, $OCH_3$, Cl or $CH_3$; $R_2$ represents H, $CF_3$, Cl or $CH_3$; X and Y independently represent CH or N;
preferably, when n=1, R represents methyl, ethyl, trifluoromethyl, n-propyl or isopropyl; $R_1$ represents H, $OCH_3$, Cl or $CH_3$; $R_2$ represents H, $CF_3$, Cl or $CH_3$; X and Y independently represent CH or N;
the preferred compounds include compounds from III-1 to III-14 as follows:
III-1  3-((2-(4-(2-methoxyphenyl)piperazin-1-yl)ethyl)methylamino)benzonitrile,
III-2 3-(methyl(2-(4-(3-trifluoromethylphenyl)piperazin-1-yl)ethyl)amino)benzonitrile,
III-3  3-((2-(4-(3-chlorophenyl)piperazin-1-yl)ethyl)methylamino)benzonitrile,
III-4  3-((2-(4-(2,3-dichlorophenyl)piperazin-1-yl)ethyl)methylamino)benzonitrile,
III-5 3-((2-(4-(2,3-dimethylphenyl)piperazin-1-yl)ethyl)methylamino)benzonitrile,
III-6  3-((2-(4-(6-chloro-5-methoxylpyrimidin-1-yl)piperazin-1-yl)ethyl)methylamino)benzonitrile,
III-7  3-((2-(4-(5-methoxypyrimidin-1-yl)piperazin-1-yl)ethyl)methylamino)benzonitrile,
III-8  3-(methyl(3-(4-(3-trifluoromethylphenyl)piperazin-1-yl)propyl)amino)benzonitrile,
III-9  3-((3-(4-(2-methoxyphenyl)piperazin-1-yl)propyl)methylamino)benzonitrile,
III-10  3-((3-(4-(3-chlorophenyl)piperazin-1-yl)propyl)methylamino)benzonitrile,
III-11  3-((3-(4-(2,3-dimethylphenyl)piperazin-1-yl)propyl)methylamino)benzonitrile,
III-12  3-((3-(4-(5-methoxylpyrimidin-1-yl)piperazin-1-yl)propyl)methylamino)benzonitrile,
III-13  3-((3-(4-(2,3-dichlorophenyl)piperazin-1-yl)propyl)methylamino)benzonitrile, or
III-14  3-((3-(4-(2-methoxyphenyl)piperazin-1-yl)propyl)ethylamino)benzonitrile.
Specific structures are shown in the table below:

| No. | Structure |
|---|---|
| III-1 | 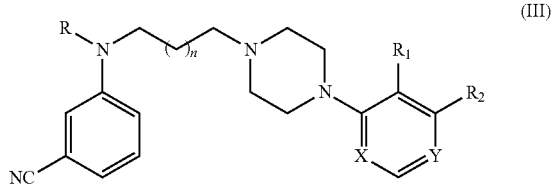 |

| No. | Structure |
|---|---|
| III-2 | (structure) |
| III-3 | (structure) |
| III-4 | (structure) |
| III-5 | (structure) |
| III-6 | (structure) |
| III-7 | (structure) |
| III-8 | (structure) |
| III-9 | (structure) |
| III-10 | (structure) |
| III-11 | (structure) |
| III-12 | (structure) |
| III-13 | (structure) |
| III-14 | (structure) | wherein, a further preferred compound includes:

III-8  3-(methyl(3-(4-(3-trifluoromethylphenyl)piperazin-1-yl)propyl)amino)benzonitrile, or III-10  3-((3-(4-(3-chlorophenyl)piperazin-1-yl)propyl)methylamino)benzonitrile.

Compounds of the present invention can be prepared according to a method described as follows:

1. Preparation of Key Intermediates

The structures of key intermediates in the general structure formula are as follows:

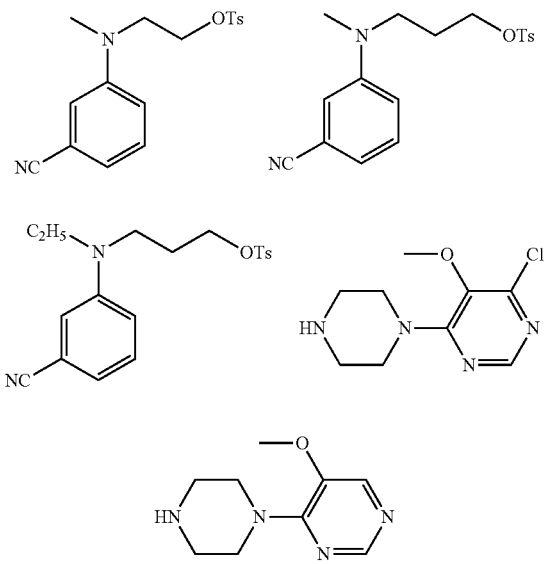 [SMILES: Cc1ccc(S(=O)(=O)OCCN(C)c2cccc(C#N)c2)cc1 ; Cc1ccc(S(=O)(=O)OCCCN(C)c2cccc(C#N)c2)cc1 ; CCN(CCCOS(=O)(=O)c1ccc(C)cc1)c1cccc(C#N)c1 ; COc1c(Cl)ncnc1N1CCNCC1 ; COc1cncnc1N1CCNCC1]

Preparation processes of the specific compounds can be found in Embodiments of the invention, the synthetic routes thereof are as follows:

(1) Synthetic routes of (2-((3-cyanophenyl)methylamino)ethyl)4-methylbenzenesulfonate, (3-((3-cyanophenyl)methylamino)propyl)4-methylbenzenesulfonate and (3-((3-cyanophenyl)ethylamino)propyl)4-methylbenzenesulfonate:

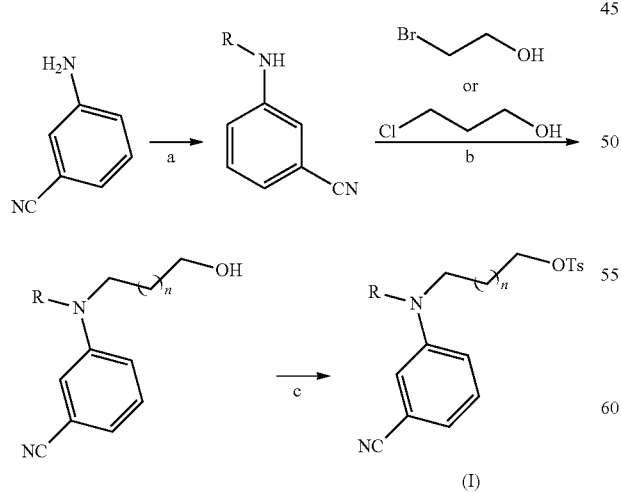

a. CH₃ONa/Polyformaldehyde or polyacetaldehyde, NaBH₄  b. CaCO₃  c. TsCl, Pyridine/CHCl₃  R: CH₃, C₂H₅

(2) Synthetic routes of 4-chloro-5-methoxy-6-(piperazin-1-yl)pyrimidine and 5-methoxy-4-(piperazin-1-yl)pyrimidine:

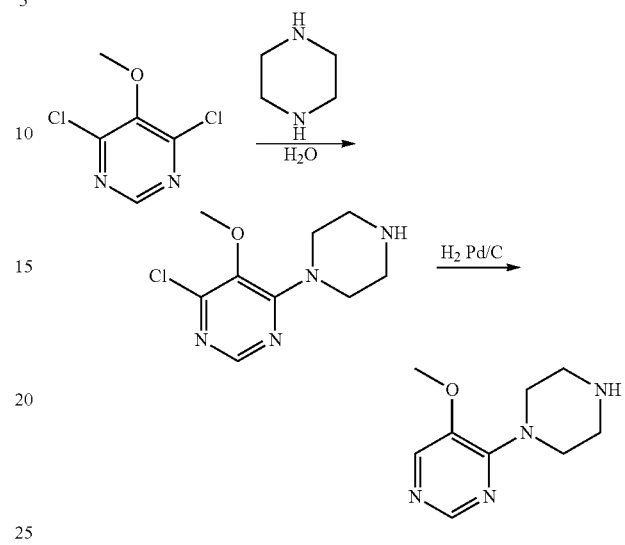

2. Preparation of Target 3-Cyanoanilinoalkylarylpiperazine Derivatives

Synthetic routes of the 3-cyanoanilinoalkylarylpiperazine derivatives of the present invention:

d: DIPEA/KI, CH₃CN
R: CH₃, C₂H₅
R₁ = H, CH₃O, Cl, CH₃
R₂ = H, CF₃, Cl, CH₃
X, Y = C, N
n = 0, 1

Condensation reaction of 3-cyanoanalinoalkylsulphonates (I) with relative aryl piperazines (II) are conducted to prepare target compounds (III), by which specific target compounds III-1 to III-14 can be obtained.

All the raw materials in above synthetic routes can be used as their commercial products.

It is demonstrated by animal experiments, the 3-cyanoanilinoalkylarylpiperazine derivative of the present invention can be used to prepare an analgesic, antidepressant, drug.

The 3-cyanoanilinoalkylarylpiperazine derivative of the present invention may also be used to prepare a drug for other central nervous system disorders, such as drug for treating neuropathic pain, vesania, anxiety, various bipolar disorder, schizophrenia, Parkinson's disease (PD), Huntington's disease (HD), Alzheimer's disease, senile dementia, Alzheimer's type dementia, allomnesia, executive function loss, vascular dementia, and other dementias, and dysfunction diseases relevant to intelligence, learning or memory.

It is found that, in in vitro assays about affinities to $5\text{-}HT_{1A}$ and $5\text{-}HT_{2A}$ receptors and 5-HT reuptake inhibition, 3-cyanoanilinoalkylarylpiperazine derivatives exhibit high affinities to $5\text{-}HT_{1A}$ and $5\text{-}HT_{2A}$ receptors and at the same time high inhibitory activity to 5-HT reuptake.

It is shown by results of animal model investigation: in rat formalin induced pain model tests, three dosages of hydrochloride of compound III-10 all exhibit obvious analgesic effect when given by intragastric administration, and it has good oral absorption; Ames test of hydrochloride of III-10 is negative; it has low acute toxicity and high therapy index, and has the potential of development as novel analgesic drugs.

In mice tail suspension test, three dosages of hydrochloride of compound III-8 all exhibit obvious antidepression effect when given by intragastric administration. It has good oral absorption, and its Ames test is negative; in single drench to mouse, hydrochloride of compound III-10 shows low acute toxicity and high therapy index, and has the potential of development as novel antidepressants.

The derivatives of the present invention can be applied as compositions to patients in need of such treatment by oral administration, injection and the like. The dosage is generally 0.02-5 mg/kg (oral administration) or 0.01-2 mg/kg (injection), and is specifically determined by doctors based on clinical results and patient's condition, age and the like.

The composition includes an effective amount of the 3-cyanoanilinoalkylarylpiperazine derivative and a pharmaceutically acceptable carrier, wherein the carrier means a traditional carrier in medicine, such as diluent, excipient like water; adhesive like cellulose derivative, gelatin, polyethylene pyrrolidone and the like; filler like starch and the like; disintegrant like calcium carbonate, sodium bicarbonate; lubricant like calcium stearate or magnesium stearate and the like. In addition, the composition could also include other adjuvants such as a flavouring agent and sweetener. Solid preparation such as tablet, powder or capsules and the like is used for an oral administration, while a parenteral solution is used for injection.

Every formulation of the composition of the present invention can be prepared using a traditional method in medical field, wherein the amount of active component is 0.1%-99.5% by weight.

The present inventors find that the derivative of the present invention has lower toxicities and low neurological side reactions.

3-cyanoanilinoalkylarylpiperazine derivative and its physiologically acceptable salt thereof of the present invention have very useful pharmaceutical properties. They exhibit effects and excellent tolerance to central nervous system, especially serotonin reuptake inhibition activity, and high affinity to $5\text{-}HT_{1A}$ and $5\text{-}HT_{2A}$ receptors. Serotonin levels in neurosynaptic gaps are adjusted through effect on multiple targets to achieve synergistic pharmaceutical effect, and hence not only the anti-neuralgia activity can be enhanced, but also the toxicity can be relatively reduced. The novel compounds of the present invention have excellent analgesic effect to various pains, including various nociceptive pains, acute pains, chronic pains, neuropathic pains, psychogenic pains and mixed pains. They specially comprise but not limited to: postoperation pains, neuropathic pains, central pains, somatic pains, visceral pains, chronic back pains, neck and waist pains, tumor pains, inflammatory pains, diabetic neuropathic pains, ischialgias, tension headaches, cluster headaches, daily chronic headaches, herpes neuropathic pains, face and oral neuropathic pains and myofascial pain syndromes, phantom limb pains, amputated limb pains and Paraplegias, toothaches, opioid resistance pains, postoperation (including cardiosurgery and mastectomy) pains, angina pectoris, pelvic pains, urogenital tract pains including cystitis, vaginal vestibule inflammation and testicular pains, early stage menstrual pain syndromes, poststroke pains, irritable bowel syndromes, tiredness and labor pains, postlabor pains, pains induced by burn and chemical injury or sun burn and bone injury pains.

3-cyanoanilinoalkylarylpiperazine derivatives of the present invention also exhibit other effects over central nervous system. In particular, they adjust the serotonin levels in neurosynaptic gaps and thus exert various physiological and pharmaceutical effects with their selective inhibition of serotonin reuptake and high affinity to $5\text{-}HT_{1A}$ and $5\text{-}HT_{2A}$ receptors. They can be used as active materials of drugs, in particular can be used in antidepression, anti-bipolar disorder, antianxiety, anti-schizophrenia, Parkinson's disease (PD), Huntington's disease (HD), Alzheimer's disease, senile dementia, Alzheimer's type dementia, allomnesia, executive function loss, vascular dementia and other dementias, and dysfunction diseases relevant to intelligence, learning or memory. And they can be used as intermediates for preparation of other pharmaceutically active compounds.

3-cyanoanilinoalkylarylpiperazine derivatives of the present invention have very useful pharmaceutical properties and excellent tolerance, particularly in use as novel analgesics, antidepressants and novel analgesic and antidepressive drugs. These compounds are novel central analgesics with serotonin level adjustment, as well as novel antidepressants with serotonin level adjustment. These compounds also have low toxic and side effect and high therapy index.

EMBODIMENTS OF THE INVENTION

Preparation of Intermediate Compounds

1. Preparation of (2-((3-cyanophenyl)methylamino)ethyl)4-methylbenzenesulfonate

1) Preparation of 3-methylaminobenzonitrile

Figure 1:
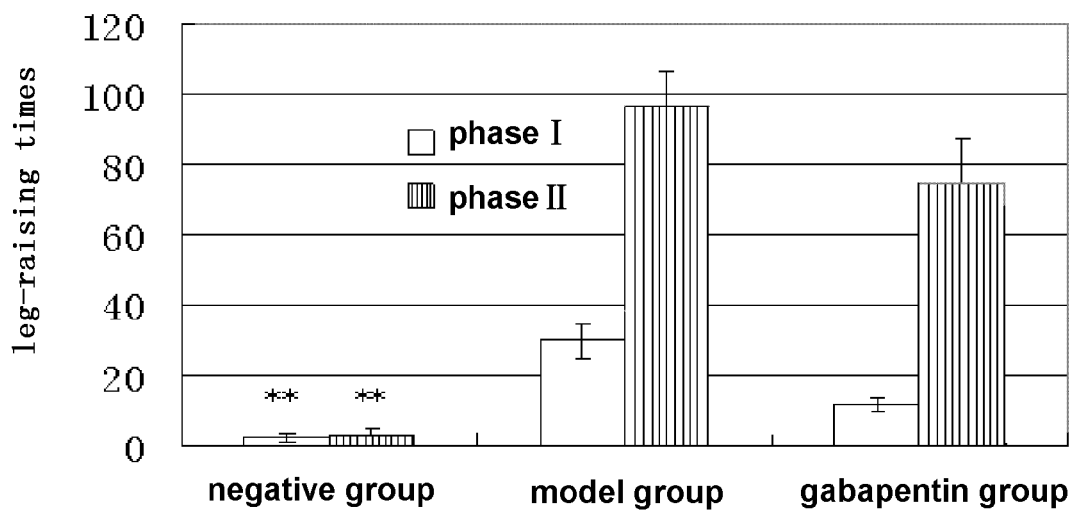
FIG. 1 is effect of positive drug gabapentin on leg-raising times of rats in formalin model.

To methanol (45 ml) is added $CH_3ONa$ (4.05 g, 75 mmol, 0.5 eq), and to this solution is dropwise added a solution of 3-aminobenzonitrile (17.70 g, 150 mmol, 1.0 eq) in methanol (60 ml). The mixture is stirred for 0.5 h. Then the reaction mixture is poured into a solution of polyformaldehyde (6.30 g, 210 mmol, 1.4 eq) in methanol (90 ml). After stirring at room temperature for 5.0 h, $NaBH_4$ (content 96%) (6.00 g, 150 mmol, 1.0 eq) is added in portions. The mixture is stirred at room temperature for 10 min, and then is refluxed at elevated temperature for 10 min. The reaction mixture is cooled under ice-water bath, and added with 10% NaOH (aq) (90 ml) and stirred for 5 min. Methanol is removed under reduced pressure, and the left aqueous solution is extracted with ethyl acetate (150 ml*2). The organic phases are combined, washed with saturated brine twice, dried over anhydrous sodium sulfate, and concentrated to yield 21.89 g of brown oily crude product. The crude product is purified by neutral alumina column chromatography (eluent: petroleum ether/$CH_2Cl_2$=2/1) to give a light yellow oily pure product (17.34 g, yield: 87.6%).

ESI-MS $[M+H]^+$: m/z 133.07

2) Preparation of 3-((2-hydroxyethyl)methylamino)benzonitrile 3-methylaminobenzonitrile (11.36 g, 86 mmol, 1.0 eq), 2-bromoethanol (43.00 g, 344 mmol, 4.0 eq) and $CaCO_3$ (34.40 g, 344 mmol, 4.0 eq) are added into water (150 ml) at room temperature, and the resulting mixture is refluxed with elevated temperature for 13.5 h, then cooled and filtered, and the aqueous solution is extracted with ethyl acetate (100 ml*3). The organic phases are combined, washed with water (20 ml*2), washed with saturated brine twice, dried over anhydrous sodium sulfate, and concentrated to give a light yellow oily crude product (11.55 g, crude yield: 76.2%). The crude product can be used directly in next step without purification.

ESI-MS $[M+H]^+$: m/z 177.10

3) Preparation of (2-((3-cyanophenyl)methylamino) ethyl)4-methylbenzenesulfonate 3-((2-hydroxyethyl)methylamino)benzonitrile (0.35 g, 2 mmol, 1.0 eq) is dissolved in chloroform (7 ml), and to this solution is added pyridine (1.15 g, 14.6 mmol, 7.3 eq) under ice-water bath condition. The reaction mixture is stirred for 3 min, and added with paratoluensulfonyl chloride (0.76 g, 4 mmol, 2.0 eq), and then the mixture is undergoing reaction at room temperature for 11 h. This system is added with 4% NaOH (aq) (15 ml) and stirred for about 10 min. The organic phase is separated, washed with water once, washed with saturated brine twice, dried over anhydrous sodium sulfate and concentrated to give a light yellow oily crude product (1.14 g). The crude product is cooled to precipitate a light yellow solid, which can be used directly in next step without purification.

ESI-MS $[M+H]^+$: m/z 331.10

2. Preparation of (3-((3-cyanophenyl)methylamino) propyl)4-methylbenzenesulfonate

1) Preparation of 3-((3-hydroxypropyl)methylamino)benzonitrile 3-methylaminobenzonitrile (17.34 g, 0.13 mol, 1.0 eq), 3-chloropropanol (49.70 g, 0.53 mol, 4.0 eq) and $CaCO_3$ (52.50 g, 0.53 mol, 4.0 eq) are added into water (230 ml) at room temperature, the mixture is refluxed at elevated temperature for 40 h, and cooled, filtered and extracted with ethyl acetate (200 ml*3). The organic phases are combined, washed with water (100 ml*2), washed with saturated brine twice, dried over anhydrous sodium sulfate and concentrated to give a light yellow oily crude product (31.08 g). The residue could be used directly in next step without purification.

ESI-MS $[M+H]^+$: m/z 191.11

2) Preparation of (3-((3-cyanophenyl)methylamino) propyl)4-methylbenzenesulfonate 3-((3-hydroxypropyl)methylamino)benzonitrile (24.90 g, 0.13 mol, 1.0 eq) is dissolved in chloroform (400 ml), and to this solution is added pyridine (75.60 g, 0.96 mol, 7.3 eq) under ice-water bath condition. The reaction mixture is stirred for 15 min, and added with paratoluensulfonyl chloride (49.90 g, 0.26 mol, 2.0 eq), and then the mixture is undergoing reaction at room temperature for 18 h. This system is added with 4% NaOH (aq) (200 ml) and is stirred for about 10 min. The organic phase is separated, washed with saturated brine twice, dried over anhydrous sodium sulfate and concentrated to give a light yellow oily crude product (51.57 g). The crude product is used directly in next step without purification.

ESI-MS $[M+H]^+$: m/z 345.12

3. Preparation of (3-((3-cyanophenyl)ethyl amino)propyl)4-methylbenzenesulfonate

1) Preparation of 3-ethylaminobenzonitrile

Sodium methoxide (4.05 g, 75 mmol) is added into methanol (45 ml) and is dissolved under stirring, and to this solution is added a solution of 3-aminobenzonitrile (17.70 g, 150 mmol) in methanol (60 ml) dropwise and the resulting mixture is stirred at room temperature for 0.5 h. Then the reaction mixture is poured into a solution of acetaldehyde (8.8 g, 200 mmol) in methanol (100 ml) and is stirred at room temperature for 5.0 h. The mixture is added with $NaBH_4$ (6.00 g, 150 mmol) in portions and is stirred at room temperature for 10 min, and then is refluxed at elevated temperature for 10 min. The reaction mixture is cooled under ice-water bath, added with 10% NaOH (aq) (90 ml) dropwise and is stirred for 5 min. Methanol is removed under reduced pressure, and the left aqueous solution is extracted with ethyl acetate (150 ml*2). The organic phases are combined, washed with saturated brine (100 ml) and separated, dried over anhydrous sodium sulfate, and concentrated to give a oily crude product (22.1 g). The crude product is purified by neutral alumina column chromatography (eluent: petroleum ether/$CH_2Cl_2$=2/1) to give a light yellow oily target product (15.4 g, yield: 70.2%).

ESI-MS $[M+H]^+$: m/z 147.08

2) Preparation of (3-((3-cyanophenyl)ethylamino) propyl)4-methylbenzenesulfonate 3-ethylaminobenzonitrile (14.6 g, 0.10 mol, 1.0 eq), 3-chloropropanol (37.8 g, 0.40 mol, 4.0 eq) and $CaCO_3$ (40.0 g, 0.40 mol, 4.0 eq) are added into water (200 ml) at room temperature, the mixture is refluxed at elevated temperature for 40 h, and cooled, filtered and extracted with ethyl acetate (200 ml*3). The organic phases are combined, washed with water (100 ml*2), washed with saturated brine twice, dried over anhydrous sodium sulfate and concentrated to give a light yellow oily crude product 3-((3-hydroxypropyl)ethylamino)benzonitrile (205.2 g). The crude product could be used directly in next step without purification. ESI-MS $[M+H]^+$: m/z 205.13

The obtained crude product (205.2 g) is dissolved in chloroform (400 ml), and to this solution is added pyridine (55.37 g, 0.70 mol, 7.0 eq) under ice-water bath condition. The reaction mixture is stirred for 15 min, and added with paratoluensulfonyl chloride (38.13 g, 0.20 mol, 2.0 eq), and then the mixture is undergoing reaction at room temperature for 18 h. This system is added with 4 wt % NaOH (200 ml) and is stirred for about 10 min and separated. The organic phase is washed with saturated brine (100 ml) and separated, dried over anhydrous sodium sulfate and concentrated to give a light yellow oily crude product (3-((3-cyanophenyl)ethylamino)propyl)4-methylbenzenesulfonate (28.4 g).

ESI-MS [M+H]$^+$: m/z 359.14

4. Preparation of 4-chloro-5-methoxy-6-(piperazin-1-yl)pyrimidine

Piperazine (6.00 g, 70 mmol, 6.25 eq) is dissolved in water (30 ml), and to this solution is added 4,6-dichloro-5-methoxypyrimidine (2.00 g, 11.2 mmol, 1.0 eq). The mixture is stirred vigorously at room temperature for 2.0 h, during which 4,6-dichloro-5-methoxypyrimidine is gradually dissolved. The aqueous phase is extracted with $CH_2Cl_2$ (25 ml*2). The extracted liquids are combined, dried over anhydrous sodium sulfate and filtered by vacuum filtration, and concentrated to give a light yellow oily crude product (2.66 g).

ESI-MS [M+H]$^+$: m/z 229.08

5. Preparation of 5-methoxy-4-(piperazin-1-yl)pyrimidine

Piperazine (20 g, 0.233 mol, 8.33 eq) is dissolved in water (100 ml), and to this solution is added 4,6-dichloro-5-methoxypyrimidine (5.00 g, 41.9 mmol, 1.0 eq). The mixture is stirred vigorously at room temperature for 2.0 h, during which 4,6-dichloro-5-methoxypyrimidine is gradually dissolved. The reaction solution is loaded into hydrogenation reactor and added with 10% Pd/C (0.66 g), and the mixture is stirred under 60 psi (0.4 Mpa) hydrogen atmosphere for 3.0 h. The mixture is filtered, extracted with $CH_2Cl_2$ (60 ml*3) for the products in the aqueous phase. Extracts are combined, dried over anhydrous sodium sulfate and filtered by vacuum filtration, and concentrated to give a crude product (5.0 g). The crude product is left to precipitate a white solid (yield: 92.6%).

ESI-MS [M+H]$^+$: m/z 195.23

General Synthetic Method for Target Compounds III-1-III-14:

Sulfonate intermediates (I) (8.8 mmol, 1.1 eq) and relative substituted arylpiperazine compounds (II) (8.0 mmol, 1.0 eq), potassium iodide (8.0 mmol, 1.0 eq) and diisopropylethylamine (32 mmol, 4.0 eq) are added into acetonitrile (50 ml). The mixture is refluxed at elevated temperature for 8-16 h, evaporated under reduced pressure to remove the solvent, and added with water (35 ml). The aqueous solution is extracted with ethyl acetate (35 ml*2) and separated. The organic phases are washed with saturated brine once, dried over anhydrous sodium sulfate, and concentrated to give a crude product. The crude product is purified by neutral alumina column chromatography (eluent: petroleum ether/ethyl acetate mixed solvent and dichloromethane) and concentrated up to dryness to give relative target compounds III-1-III-14.

Then III-1-III-14 are dissolved in ethyl acetate (30 ml), and $HCl/C_2H_5OH$ (3N) is used to adjust the PH to PH<3. A solid is precipitated and filtered, which is recrystallized with ethyl acetate/ethanol solvent to give hydrochloride of the target compounds (III-1-III-14). The yields are 40-70%.

Example 1

Preparation of hydrochloride, hydrobromide and sulfate of 3-((2-(4-(2-methoxyphenyl)piperazin-1-yl)ethyl)methylamino)benzonitrile (III-1)

(2-((3-cyanophenyl)methylamino)ethyl)4-methylbenzenesulfonate (2.90 g, 8.8 mmol, 1.1 eq), 2-methoxyphenylpiperazine (1.54 g, 8.0 mmol, 1.0 eq), potassium iodide (1.33 g, 8.0 mmol, 1.0 eq) and diisopropylethylamine (4.10 g, 32 mmol, 4.0 eq) are added into 50 ml of acetonitrile. The mixture is refluxed for 12 h and the raw materials are reacted completely. The solvent is removed under reduced pressure, and water (35 ml) is added to the residue. The aqueous solution is extracted with ethyl acetate (35 ml*2) and separated. The organic phase is washed with saturated brine once, dried over anhydrous sodium sulfate, and concentrated to give a brown oily crude product (3.06 g). The crude product is purified by neutral alumina column chromatography, with petroleum ether/ethyl acetate=3:1 (volume ratio) as an eluent at first and then dichloromethane as an eluent, to give a powdery compound (III-1) (1.70 g, yield: 60.5%).

1.70 g of above solid is dissolved in ethyl acetate (25 ml), and to this solution HCl/ethyl acetate (3M) solution (9.7 ml) is added dropwise. A white solid is precipitated. This system is heated till reflux, and added with anhydrous ethanol (4 ml) and refluxed for 15 min. The heating is stopped, and the mixture is cooled to room temperature and filtered to give a white powdery hydrochloride of compound (III-1) (2.00 g, yield: 97.6%).

Elemental analysis: $C_{21}H_{26}N_4O.2HCl$ (theoretical value %: C, 59.57; H, 6.67; N, 13.23; Cl, 16.75; experimental value % C, 59.76; H, 6.74; N, 13.28; Cl, 16.84)

ESI-MS [M+H]$^+$: m/z 351.22

$^1$H-NMR (400 MHz), DMSO-d$_6$: δ 2.97 (s, 3H), 3.10-3.40 (m, 4H), 3.26-3.28 (m, 2H), 3.51-5.54 (m, 4H), 3.80 (s, 3H), 3.90 (t, 2H), 6.91 (t, 1H), 6.99 (d, 2H), 7.04 (t, 2H), 7.18 (d, 1H), 7.19 (s, 1H), 7.36 (tt, 1H), 11.7 (br, 1H, HCl)

Compound (III-1) (1.75 g) prepared using above method is dissolved in ethyl acetate (25 ml), and to this solution is added dropwise hydrogen bromide/ethyl acetate (3M) solution (10.0 ml). A white solid is precipitated under stirring at room temperature. The mixture is heated till reflux, and added with 5 ml of anhydrous ethanol and refluxed for 15 min. The heating is stopped, and the mixture is cooled to room temperature and filtered to give hydrobromide of compound (III-1), which is a white powdery solid (2.10 g, yield: 82.0%).

ESI-MS [M+H]$^+$: m/z 351.22

Elemental analysis: $C_{21}H_{26}N_4O.2HBr$ (theoretical value %: C, 49.24; H, 5.51; N, 10.94; Br, 31.20; experimental value % C, 49.33; H, 5.67; N, 10.88; Br, 31.26)

Compound (III-1) (1.75 g) prepared using above method is dissolved in ethanol (25 ml), and to this solution is added dropwise diluted aqueous solution of sulfuric acid (3M) (10.0 ml). A white solid is precipitated under stirring at room temperature, and is filtered to give a crude product. The crude product is recrystallized with 95% (weight ratio) ethanol, filtered and dried to give sulfate of compound (III-1), which is white powdery solid (2.06 g, yield: 75.4%).

ESI-MS [M+H]$^+$: m/z 351.22

Elemental analysis: $C_{21}H_{26}N_4O.2H_2SO_4$ (theoretical value %: C, 46.14; H, 5.53; N, 10.25; S, 11.73; experimental value % C, 46.23; H, 5.67; N, 10.24; S, 11.62)

Example 2

Preparation of hydrochloride of 3-(methyl(2-(4-(3-trifluoromethylphenyl)piperazin-1-yl)ethyl)amino)benzonitrile (III-2)

(2-((3-cyanophenyl)methylamino)ethyl)4-methylbenzenesulfonate (2.79 g, 8.5 mmol, 1.1 eq), 3-trifluoromethylphenylpiperazine (1.77 g, 7.6 mmol, 1.0 eq), potassium iodide (1.26 g, 7.6 mmol, 1.0 eq) and diisopropylethylamine (3.90 g, 30.4 mmol, 4.0 eq) are added into acetonitrile (46 ml). The mixture is refluxed for 12 h, and the raw materials are reacted completely. The solvent is removed under reduced pressure, and water (35 ml) is added to the residue. The aqueous solution is extracted with ethyl acetate (30 ml*2) and separated. The organic phase is washed with saturated brine once, dried over anhydrous sodium sulfate, and concentrated to give a brown oily crude product (3.6 g). The crude product is purified by neutral alumina column chromatography, with petroleum ether/ethyl acetate=3:1 (volume ratio) as an eluent at first and then dichloromethane as an eluent, to give a light yellow oily compound (III-2) (2.20 g, yield: 73.8%).

Above light yellow oily compound (2.20 g) is dissolved in ethyl acetate (30 ml), and to this solution is added HCl/ethyl acetate (3M) solution (5.67 ml) dropwise. A white solid is precipitated. This system is heated till reflux and added with anhydrous ethanol (4 ml) and refluxed for 15 min. The heating is stopped, and the mixture is cooled to room temperature and filtered to give a white powdery solid (1.42 g). The total yield of the two steps is 54.4%.

ESI-MS $[M+H]^+$: m/z 389.20
$^1$H-NMR (400 MHz), DMSO-$d_6$: δ 2.93 (s, 3H), 3.27-3.29 (m, 2H), 3.00-3.40 (m, 4H), 3.40-3.70 (m, 4H), 3.78 (t, 2H), 7.05 (d, 1H), 7.15 (d, 1H), 7.16 (d, 1H), 7.19 (s, 1H), 7.26 (s, 1H), 7.29 (d, 1H), 7.36 (tt, 1H), 7.47 (t, 1H), 11.8 (br, 1H)

Example 3

Preparation of hydrochloride of 3-((2-(4-(3-chlorophenyl)piperazin-1-yl)ethyl)methylamino)benzonitrile (III-3)

(2-((3-cyanophenyl)methylamino)ethyl)4-methylbenzenesulfonate (4.06 g, 12 mmol, 1.1 eq), 3-chlorophenylpiperazine (2.20 g, 11 mmol, 1.0 eq), potassium iodide (1.86 g, 11 mmol, 1.0 eq) and diisopropylethylamine (5.74 g, 45 mmol, 4.0 eq) are added in acetonitrile (70 ml). The mixture is refluxed for 12 h, and the raw materials are reacted completely. The solvent is removed under reduced pressure, and water (40 ml) is added to the residue. The aqueous solution is extracted with ethyl acetate (40 ml*2) and separated. The organic phase is washed with saturated brine once, dried over anhydrous sodium sulfate, and concentrated to give a brown oily crude product (4.01 g). The crude product is purified by neutral alumina column chromatography, with petroleum ether/ethyl acetate=3:1 (volume ratio) as an eluent at first and then dichloromethane as an eluent, to give a light yellow oily compound (III-3) (2.14 g, yield: 53.9%).

Above light yellow oily compound (2.14 g) is dissolved in ethyl acetate (30 ml), and to this solution is added HCl/ethyl acetate (3M) solution (6 ml) dropwise. A white solid is precipitated. This system is heated till reflux and added with anhydrous ethanol (4 ml) and refluxed for 15 min. The heating is stopped, and the mixture is cooled to room temperature and filtered to give a light pink powdery solid (1.88 g). The total yield of the two steps is 72.9%.

ESI-MS $[M+H]^+$: m/z 355.16
$^1$H-NMR (400 MHz), DMSO-$d_6$: δ 2.97 (s, 3H), 3.10-3.30 (m, 4H), 3.28 (t, 2H), 3.56 (s, 2H), 3.86 (s, 2H), 3.92 (t, 2H), 6.85 (d, 1H), 6.95 (dd, 1H), 7.03 (d, 1H), 7.04 (s, 1H), 7.17 (d, 1H), 7.19 (s, 1H), 7.25 (t, 1H), 7.35 (tt, 1H), 12.0 (br, 1H)

Example 4

Preparation of hydrochloride of 3-((2-(4-(2,3-dichlorophenyl)piperazin-1-yl)ethyl)methylamino)benzonitrile (III-4)

(2-((3-cyanophenyl)methylamino)ethyl)4-methylbenzenesulfonate (3.52 g, 11 mmol, 1.1 eq), 2,3-dichlorophenylpiperazine (2.24 g, 9.7 mmol, 1.0 eq), potassium iodide (1.61 g, 9.7 mmol, 1.0 eq) and diisopropylethylamine (4.95 g, 39 mmol, 4.0 eq) are added in acetonitrile (62 ml). The mixture is refluxed for 12 h, and the raw materials are reacted completely. The solvent is removed under reduced pressure, and water (40 ml) is added to the residue. The aqueous solution is extracted with ethyl acetate (40 ml*2) and separated. The organic phase is washed with saturated brine once, dried over anhydrous sodium sulfate, and concentrated to give a brown oily crude product (4.13 g). The crude product is purified by neutral alumina column chromatography, with petroleum ether/ethyl acetate=3:1 (volume ratio) as an eluent at first and then dichloromethane as an eluent, to give a light yellow oily pure product (III-4) (2.00 g, yield: 53.1%).

Above light yellow oily compound (2.00 g) is dissolved in ethyl acetate (25 ml), and to this solution is added HCl/ethyl acetate (3M) solution (5.14 ml) dropwise. A white solid is precipitated. This system is heated till reflux and added with anhydrous ethanol (4 ml) and refluxed for 15 min. The heating is stopped, and the mixture is cooled to room temperature and filtered to give a light pink powdery solid (1.62 g). The total yield of the two steps is 68.4%.

ESI-MS $[M+H]^+$: m/z 389.12
$^1$H-NMR (400 MHz), DMSO-$d_6$: δ 2.97 (s, 3H), 3.20-3.40 (m, 4H), 3.31-3.33 (m, 2H), 3.42 (s, 2H), 3.60 (s, 2H), 3.82 (t, 2H), 7.03 (d, 1H), 7.16-7.20 (m, 3H), 7.33-7.37 (m, 3H), 11.6 (br, 1H, HCl)

Example 5

Preparation of hydrochloride of 3-((2-(4-(2,3-dimethylphenyl)piperazin-1-yl)ethyl)methylamino)benzonitrile (III-5)

(2-((3-cyanophenyl)methylamino)ethyl)4-methylbenzenesulfonate (4.34 g, 13 mmol, 1.1 eq), 2,3-dimethylphenylpiperazine (2.27 g, 12 mmol, 1.0 eq), potassium iodide (1.98 g, 12 mmol, 1.0 eq) and diisopropylethylamine (6.10 g, 48 mmol, 4.0 eq) are added in acetonitrile (75 ml). The mixture is refluxed for 12 h, and the raw materials are reacted completely. The solvent is removed under reduced pressure, and water (45 ml) is added to the residue. The aqueous solution is extracted with ethyl acetate (45 ml*2) and separated. The organic phase is washed with saturated brine once, dried over anhydrous sodium sulfate, and concentrated to give a brown solid crude product (3.83 g). The crude product is purified by neutral alumina column chromatography, with petroleum ether/ethyl acetate=3:1 (volume ratio) as an eluent at first and then dichloromethane as an eluent, to give a light yellow solid (III-5) (1.82 g, yield: 43.8%).

Above light yellow solid (1.82 g) is dissolved in ethyl acetate (25 ml), and to this solution is added HCl/ethyl acetate (3M) solution (5.23 ml) dropwise. A white solid is precipitated. This system is heated till reflux and added with anhydrous ethanol (4 ml) and refluxed for 15 min. The heating is stopped, and the mixture is cooled to room temperature and filtered to give a white powdery solid (1.77 g). The total yield of the two steps is 80.5%.

ESI-MS [M+H]$^+$: m/z 349.23

$^1$H-NMR (400 MHz), DMSO-d$_6$: δ 2.18 (s, 3H), 2.22 (s, 3H), 2.99 (s, 3H), 3.09-3.11 (m, 4H), 3.30 (t, 2H), 3.29-3.31 (m, 2H), 3.56-3.58 (m, 2H), 3.85 (t, 2H), 6.92 (t, 2H), 7.05 (d, 1H), 7.08 (d, 1H), 7.20 (d, 1H), 7.21 (s, 1H), 7.36 (t, 1H), 11.9 (br, 1H, HCl)

Example 6

Preparation of hydrochloride of 3-((2-(4-(6-chloro-5-methoxylpyrimidin-1-yl)piperazin-1-yl)ethyl)methylamino)benzonitrile (III-6)

(2-((3-cyanophenyl)methylamino)ethyl)4-methylbenzenesulfonate (3.38 g, 10.2 mmol, 1.1 eq), 4-chloro-5-methoxy-6-(piperazin-1-yl)pyrimidine (2.10 g, 9.3 mmol, 1.0 eq), potassium iodide (1.54 g, 9.3 mmol, 1.0 eq) and diisopropylethylamine (4.73 g, 37.2 mmol, 4.0 eq) are added in acetonitrile (56 ml). The mixture is refluxed for 12 h, and the raw materials are reacted completely. The solvent is removed under reduced pressure, and water (45 ml) is added to the residue. The aqueous solution is extracted with ethyl acetate (45 ml*2) and separated. The organic phase is washed with saturated brine once, dried over anhydrous sodium sulfate, and concentrated to give a brown oily crude product (3.83 g). The crude product is purified by neutral alumina column chromatography, with petroleum ether/ethyl acetate=3:1 (volume ratio) as an eluent at first and then dichloromethane as an eluent, to give a light yellow oily crude product (III-6) (1.76 g, yield: 49.6%).

Above light yellow oily crude product (1.76 g) is dissolved in ethyl acetate (25 ml), and to this solution is added HCl/ethyl acetate (3M) solution (4.55 ml) dropwise. A white solid is precipitated. This system is heated till reflux and added with anhydrous ethanol (4 ml) and refluxed for 15 min. The heating is stopped, and the mixture is cooled to room temperature and filtered to give a white powdery solid (1.40 g). The total yield of the two steps is 67%.

ESI-MS [M+H]$^+$: m/z 387.16

$^1$H-NMR (400 MHz), DMSO-d$_6$: δ 2.93 (s, 3H), 3.26-3.29 (m, 4H), 3.60-3.62 (m, 4H), 3.74 (s, 3H), 3.88 (t, 2H), 4.59 (s, 2H), 7.15 (d, 2H), 7.17 (s, 1H), 7.36 (d, 1H), 8.27 (s, 1H), 11.9 (br, 1H, HCl)

Example 7

Preparation of hydrochloride of 3-((2-(4-(5-methoxypyrimidin-1-yl)piperazin-1-yl)ethyl)methylamino)benzonitrile (III-7)

(2-((3-cyanophenyl)methylamino)ethyl)4-methylbenzenesulfonate (3.93 g, 11.9 mmol, 1.1 eq), 5-methoxy-4-(piperazin-1-yl)pyrimidine (2.10 g, 10.8 mmol, 1.0 eq), potassium iodide (1.80 g, 10.8 mmol, 1.0 eq) and diisopropylethylamine (5.51 g, 43.3 mmol, 4.0 eq) are added in acetonitrile (65 ml). The mixture is refluxed for 12 h, and the raw materials are reacted completely. The solvent is removed under reduced pressure, and water (45 ml) is added to the residue. The aqueous solution is extracted with ethyl acetate (45 ml*2) and separated. The organic phase is washed with saturated brine once, dried over anhydrous sodium sulfate, and concentrated to give a brown oily crude product (4.37 g). The crude product is purified by neutral alumina column chromatography, with petroleum ether/ethyl acetate=3:1 (volume ratio) as an eluent at first and then dichloromethane as an eluent, to give a light yellow oily compound (III-7) (1.54 g, yield: 40.4%).

Above light yellow oily compound (1.54 g) is dissolved in ethyl acetate (25 ml), and to this solution is added HCl/ethyl acetate (3M) solution (4.4 ml) dropwise. A white solid is precipitated. This system is heated till reflux and added with anhydrous ethanol (4 ml) and refluxed for 15 min. The heating is stopped, and the mixture is cooled to room temperature and filtered to give a white powdery solid (1.00 g). The total yield of the two steps is 53.8%.

ESI-MS [M+H]$^+$: m/z 353.20

$^1$H-NMR (400 MHz), DMSO-d$_6$: δ 2.97 (s, 3H), 3.25 (t, 2H), 3.28-3.30 (m, 2H), 3.55-3.57 (m, 4H), 3.90 (t, 2H), 3.93 (s, 3H), 4.59-4.61 (m, 2H), 7.05 (s, 1H), 7.16 (d, 1H), 7.18 (s, 1H), 7.36 (t, 1H), 8.23 (s, 1H), 8.66 (s, 1H), 12.2 (br, 1H, HCl)

Example 8

Preparation of hydrochloride of 3-(methyl(3-(4-(3-trifluoromethylphenyl)piperazin-1-yl)propyl)amino)benzonitrile (III-8)

3-((3-chloropropyl)methylamino)benzonitrile (2.38 g, 11.43 mmol, 1.1 eq), 3-trifluoromethylphenylpiperazine (2.39 g, 10.4 mmol, 1.0 eq), potassium iodide (1.73 g, 10.4 mmol, 1.0 eq) and diisopropylethylamine (5.36 g, 41.6 mmol, 4.0 eq) are added in acetonitrile (64 ml). The mixture is refluxed for 15 h, and the raw materials are reacted completely. The solvent is removed under reduced pressure, and water (35 ml) is added to the residue. The aqueous solution is extracted with ethyl acetate (35 ml*2) and separated. The organic phase is washed with saturated brine once, dried over anhydrous sodium sulfate, and concentrated to give a brown oily crude product (3.00 g). The crude product is purified by neutral alumina column chromatography, with petroleum ether/ethyl acetate=3:1 (volume ratio) as an eluent at first and then dichloromethane as an eluent, to give a light yellow oily compound (III-8) (1.19 g, yield: 28.5%).

Above light yellow oily compound (1.37 g) is dissolved in ethyl acetate (25 ml), and to this solution is added HCl/ethyl acetate (3M) solution (3.4 ml) dropwise. A white solid is precipitated. This system is heated till reflux and added with anhydrous ethanol (4 ml) and refluxed for 15 min. The heating is stopped, and the mixture is cooled to room temperature and filtered to give a white powdery solid (0.86 g). The total yield of the two steps is 53.1%.

ESI-MS [M+H]$^+$: m/z 403.21

$^1$H-NMR (400 MHz), DMSO-d$_6$: δ 2.04 (q, 2H), 2.94 (s, 3H), 3.10-3.15 (m, 4H), 3.33 (t, 2H), 3.46 (t, 2H), 3.53 (d, 2H), 3.90 (d, 2H), 7.01 (d, 1H), 7.09 (dd, 1H), 7.11 (s, 1H), 7.14 (d, 1H), 7.24 (s, 1H), 7.27 (d, 1H), 7.35 (t, 1H), 7.46 (t, 1H), 11.6 (br, 1H, HCl)

Example 9

Preparation of hydrochloride of 3-((3-(4-(2-methoxyphenyl)piperazin-1-yl)propyl)methylamino)benzonitrile (III-9)

3-((3-chloropropyl)methylamino)benzonitrile (3.67 g, 17.6 mmol, 1.1 eq), 2-methoxyphenylpiperazine (3.06 g, 16 mmol, 1.0 eq), potassium iodide (2.66 g, 16 mmol, 1.0 eq) and diisopropylethylamine (8.25 g, 64 mmol, 4.0 eq) are added in acetonitrile (80 ml). The mixture is refluxed for 15 h, and the raw materials are reacted completely. The solvent is removed under reduced pressure, and water (55 ml) is added to the residue. The aqueous solution is extracted with ethyl acetate (55 ml*2) and separated. The organic phase is washed with saturated brine once, dried over anhydrous sodium sulfate, and concentrated to give a brown oily crude product (3.56 g). The crude product is purified by neutral alumina column chromatography, with petroleum ether/ethyl acetate=3:1 (volume ratio) as an eluent at first and then dichloromethane as an eluent, to give a light yellow oily compound (III-9) (2.50 g, yield: 43.1%).

Above light yellow oily compound (2.50 g) is dissolved in ethyl acetate (35 ml), and to this solution is added HCl/ethyl acetate (3M) solution (6.8 ml) dropwise. A white solid is precipitated. This system is heated till reflux and added with anhydrous ethanol (6 ml) and refluxed for 15 min. The heating is stopped, and the mixture is cooled to room temperature and filtered to give a light pink powdery solid (2.24 g). The total yield of the two steps is 74.7%.

ESI-MS [M+H]$^+$: m/z 365.23
$^1$H-NMR (400 MHz), DMSO-d$_6$: δ 1.96 (q, 2H), 2.91 (s, 3H), 2.98 (d, 2H), 3.11-3.18 (m, 4H), 3.53-3.40 (m, 6H), 3.79 (s, 3H), 6.88-7.06 (m, 5H), 7.07-7.09 (m, 2H), 7.34 (t, 1H), 11.4 (br, 1H, HCl)

Example 10

Preparation of hydrochloride of 3-((3-(4-(3-chlorophenyl)piperazin-1-yl)propyl)methylamino)benzonitrile (III-10)

3-((3-chloropropyl)methylamino)benzonitrile (3.06 g, 14.7 mmol, 1.1 eq), 3-chlorophenylpiperazine (2.62 g, 13.3 mmol, 1.0 eq), potassium iodide (2.20 g, 13.3 mmol, 1.0 eq) and diisopropylethylamine (6.86 g, 53.2 mmol, 4.0 eq) are added in acetonitrile (65 ml). The mixture is refluxed for 15 h, and the raw materials are reacted completely. The solvent is removed under reduced pressure, and water (45 ml) is added to the residue. The aqueous solution is extracted with ethyl acetate (45 ml*2) and separated. The organic phase is washed with saturated brine once, dried over anhydrous sodium sulfate, and concentrated to give a brown oily crude product (3.73 g). The crude product is purified by neutral alumina column chromatography, with petroleum ether/ethyl acetate=3:1 (volume ratio) as an eluent at first and then dichloromethane as an eluent, to give a light yellow oily compound (III-10) (2.67 g, yield: 54.5%).

Above light yellow oily compound (2.67 g, 7.2 mmol, 1.0 eq) is dissolved in ethyl acetate (9 ml), and to this solution is added HCl/ethyl acetate (3M) solution (7.2 ml) dropwise. A white solid is precipitated. This system is stirred at room temperature for 10 min, heated till reflux and added with anhydrous ethanol (2 ml) and refluxed for 15 min. The heating is stopped, and the mixture is cooled to room temperature and filtered to give a light pink powdery solid (2.12 g). The total yield of the two steps is 66.25%.

ESI-MS [M+H]$^+$: m/z 369.19
$^1$H-NMR (400 MHz), DMSO-d$_6$: δ 2.02 (q, 2H), 2.94 (s, 3H), 3.07-3.17 (m, 4H), 3.29 (t, 2H), 3.46 (t, 2H), 3.50 (d, 2H), 3.84 (d, 2H), 6.86 (d, 1H), 6.95 (dd, 1H), 7.00 (d, 1H), 7.03 (s, 1H), 7.06 (dd, 1H), 7.09 (s, 1H), 7.25 (t, 1H), 7.34 (t, 1H), 11.6 (br, 1H, HCl)

Example 11

Preparation of hydrochloride of 3-((3-(4-(2,3-dimethylphenyl)piperazin-1-yl)propyl)methylamino)benzonitrile (III-11)

3-((3-chloropropyl)methylamino)benzonitrile (3.54 g, 17 mmol, 1.1 eq), 2,3-dimethylphenylpiperazine (2.93 g, 15.4 mmol, 1.0 eq), potassium iodide (2.56 g, 15.4 mmol, 1.0 eq) and diisopropylethylamine (7.80 g, 61.6 mmol, 4.0 eq) are added in acetonitrile (70 ml). The mixture is refluxed for 15 h, and the raw materials are reacted completely. The solvent is removed under reduced pressure, and water (55 ml) is added to the residue. The aqueous solution is extracted with ethyl acetate (55 ml*2) and separated. The organic phase is washed with saturated brine once, dried over anhydrous sodium sulfate, and concentrated to give a brown oily crude product (3.74 g). The crude product is purified by neutral alumina column chromatography, with petroleum ether/ethyl acetate=3:1 (volume ratio) as an eluent at first and then dichloromethane as an eluent, to give a light yellow oily compound (III-11) (2.82 g, yield: 50.5%).

Above light yellow oily compound (2.82 g, 7.8 mmol, 1.0 eq) is dissolved in ethyl acetate (20 ml), and to this solution is added HCl/ethyl acetate (3M) solution (7.8 ml) dropwise. A white solid is precipitated. This system is stirred at room temperature for 10 min, heated till reflux and added with anhydrous ethanol (2 ml) and refluxed for 5 min. The heating is stopped, and the mixture is cooled to room temperature and filtered to give a white powdery solid (2.27 g). The total yield of the two steps is 70.0%.

ESI-MS [M+H]$^+$: m/z 363.25
$^1$H-NMR (400 MHz), DMSO-d$_6$: δ 2.04 (q, 2H), 2.17 (s, 3H), 2.22 (s, 3H), 2.95 (s, 3H), 3.06-3.30 (m, 8H), 3.45-3.52 (m, 4H), 6.89 (d, 1H), 6.92 (d, 1H), 7.00 (d, 1H), 7.04-7.09 (m, 3H), 7.34 (t, 1H), 11.4 (br, 1H, HCl)

Example 12

Preparation of hydrochloride of 3-((3-(4-(5-methoxylpyrimidin-1-yl)piperazin-1-yl)propyl)methylamino)benzonitrile (III-12)

3-((3-chloropropyl)methylamino)benzonitrile (2.52 g, 12.1 mmol, 1.1 eq), 5-methoxy-4-(piperazin-1-yl)pyrimidine (2.13 g, 10.9 mmol, 1.0 eq), potassium iodide (1.80 g, 10.9 mmol, 1.0 eq) and diisopropylethylamine (5.51 g, 43.3 mmol, 4.0 eq) are added in acetonitrile (65 ml). The mixture is refluxed for 12 h, and the raw materials are reacted completely. The solvent is removed under reduced pressure, and water (30 ml) is added to the residue. The aqueous solution is extracted with ethyl acetate (35 ml*3) and separated. The organic phase is washed with saturated brine twice, dried over anhydrous sodium sulfate, and concentrated to give a light yellow oily crude product (2.06 g). The crude product is purified by neutral alumina column chromatography, with petroleum ether/ethyl acetate=3:1 (volume ratio) as an eluent at first and then dichloromethane as an eluent, to give a light yellow oily compound (III-12) (1.57 g, yield: 39.1%).

Above light yellow oily compound (1.57 g, 4.29 mmol, 1.0 eq) is dissolved in ethyl acetate (20 ml), and to this solution is added HCl/ethyl acetate (3M) solution (4.29 ml) dropwise. A white solid is precipitated. This system is heated till reflux and added with anhydrous ethanol (2 ml) and refluxed for 15 min. The heating is stopped, and the mixture is cooled to room temperature and filtered to give a white powdery solid (0.80 g). The total yield of the two steps is 42.6%.

ESI-MS [M+H]$^+$: m/z 367.22
$^1$H-NMR (400 MHz), DMSO-d$_6$: δ 2.00 (q, 2H), 2.93 (s, 3H), 3.13 (t, 2H), 3.20 (s, 2H), 3.47 (t, 2H), 3.60 (s, 4H), 3.83 (s, 2H), 3.93 (s, 3H), 4.97 (s, 2H), 6.99 (d, 1H), 7.09 (d, 1H), 7.11 (s, 1H), 7.34 (t, 1H), 8.21 (s, 1H), 8.69 (s, 1H), 12.1 (br, 1H, HCl)

Example 13

Preparation of hydrochloride of 3-((3-(4-(2,3-dichlorophenyl)piperazin-1-yl)propyl)methylamino)benzonitrile (III-13)

3-((3-chloropropyl)methylamino)benzonitrile (2.90 g, 14 mmol, 1.1 eq) 2,3-dichlorophenylpiperazine (2.93 g, 12.7 mmol, 1.0 eq), potassium iodide (2.10 g, 12.7 mmol, 1.0 eq) and diisopropylethylamine (6.46 g, 50.8 mmol, 4.0 eq) are added in acetonitrile (77 ml). The mixture is refluxed for 12 h, and the raw materials are reacted completely. The solvent is removed under reduced pressure, and water (40 ml) is added to the residue. The aqueous solution is extracted with ethyl acetate (40 ml*2) and separated. The organic phase is washed with saturated brine once, dried over anhydrous sodium sulfate, and concentrated to give a brown oily crude product (4.69 g). The crude product is purified by neutral alumina column chromatography, with petroleum ether/ethyl acetate=3:1 (volume ratio) as an eluent at first and then dichloromethane as an eluent, to give a light yellow oily compound (III-13) (3.80 g, yield: 74.4%).

Above light yellow oily compound (3.80 g) is dissolved in ethyl acetate (20 ml), and to this solution is added HCl/ethyl acetate (3M) solution (9.3 ml) dropwise. A white solid is precipitated. This system is heated till reflux and added with anhydrous ethanol (3 ml) and refluxed for 5 min. The heating is stopped, and the mixture is cooled to room temperature and filtered to give a white powdery solid (2.66 g). The total yield of the two steps is 59.2%.

ESI-MS [M+H]$^+$: m/z 403.14

$^1$H-NMR (400 MHz), DMSO-$d_6$: δ 2.04 (q, 2H), 2.95 (s, 3H), 3.15-3.17 (m, 4H), 3.31 (t, 2H), 3.39 (d, 2H), 3.48 (q, 2H), 3.56 (d, 2H), 7.02 (d, 1H), 7.15-7.17 (m, 3H), 7.32-7.38 (m, 3H), 11.7 (br, 1H, HCl)

Example 14

Preparation of hydrochloride of 3-((3-(4-(2-methoxyphenyl)piperazin-1-yl)propyl)ethylamino)benzonitrile (III-14)

(3-((3-cyanophenyl)ethylamino)propyl)4-methylbenzenesulfonate (3.94 g, 11 mmol, 1.1 eq), 2-methoxyphenylpiperazine (1.92 g, 10 mmol, 1.0 eq), potassium iodide (1.66 g, 10 mmol, 1.0 eq) and diisopropylethylamine (5.17 g, 40 mmol, 4.0 eq) are added in acetonitrile (70 ml). The mixture is refluxed for 12 h, and the raw materials are reacted completely. The solvent is removed under reduced pressure, and water (40 ml) is added to the residue. The aqueous solution is extracted with ethyl acetate (40 ml*2) and separated. The organic phase is washed with saturated brine once, dried over anhydrous sodium sulfate, and concentrated to give an oily compound. The oily compound is purified by neutral alumina column chromatography, with dichloromethane/methanol=100:1 as an eluent, to give a light yellow oily compound (III-14) (2.89 g, yield: 76.4%).

Above compound is dissolved in ethyl acetate (20 ml), and to this solution is added HCl/ethyl acetate (3M) solution (9.0 ml) dropwise. A white solid is precipitated. This system is added with anhydrous ethanol (2 ml) and refluxed for 5 min. The mixture is cooled to room temperature and filtered to give a white solid (2.45 g). The total yield of the two steps is 54.3%.

ESI-MS [M+H]$^+$: m/z 379.24

$^1$H-NMR (400 MHz), DMSO-$d_6$: δ t, 3H 1.93-1.97 (m, 2H), 2.95 (q, 2H), 2.98-3.00 (m, 2H), 3.11-3.18 (m, 4H), 3.53-3.40 (m, 6H), 3.79 (s, 3H), 6.88-7.07 (m, 5H), 7.09-7.11 (m, 2H), 7.34 (t, 1H), 11.4 (br, 1H, HCl).

Example 15-1

| Tablet: | the derivatives of the present invention | 25 mg |
|---|---|---|
| | sucrose | 155 mg |
| | corn starch | 65 mg |
| | magnesium stearate | 5 mg |

Preparation method: the active ingredients, sucrose and corn starch are mixed, humidified with water and stirred uniformly, and dried, crushed and sieved. The sieved part are added with magnesium stearate and mixed uniformly, and tableted. Each tablet has the weight of 250 mg with the active ingredients contents of 25 mg.

Example 15-2

| Injection: | the derivatives of the present invention | 10 mg |
|---|---|---|
| | injection water | 90 mg |

Preparation method: the active ingredients are dissolved in injection water and mixed uniformly, and filtered. The resulting solution is dispensed into ampoules under sterile condition, 10 mg/bottle, and the content of active ingredients is 1 mg/bottle.

Example 16

In vitro binding of compounds to 5-HT$_{1A}$ and 5-HT$_{2A}$ receptors and inhibition effect of compounds to serotonin reuptake

1) In Vitro Binding Test of Compounds to 5-HT$_{1A}$ and 5-HT$_{2A}$ Receptors

1. Experimental Materials

Animals: clean grade SD rats, female and male, 250-300 g, purchased from Nanjing QingLongshan animal breeding center.

Radioligand: [$^3$H]-8-OH-DPAT, [$^3$H]-Ketanserin, purchased from PerkinElmer company; 5-HT and Methysergide, purchased from Sigma company.

GF/C glass fiber filter paper, purchased from Whatman company.

Tris, import-packaged.

PPO, POPOP, purchased from Sigma company.

Toluene, purchased from Shanghai SuYi chemical reagent limited corporation.

Positive drug: aripiprazole.

Instrument: Liquid Scintillation counter, purchased from Hidex company.

2. Experimental Methods

2.1 Preparation of Solutions

Preparation of 5-HT$_{2A}$ buffer solution: Tris (6.05 g) is dissolved in ultrapure water (1000 ml). PH is adjusted to 7.4 with HCl. Tris-HCl buffer solution (0.05M) is used.

Preparation of 5-HT$_{1A}$ buffer solution: Tris-HCl buffer solution (0.05M, 1000 ml) is added with certain amount of ascorbic acid, pargyline and CaCl$_2$, to give final concentrations of 0.1%(ascorbic acid), 10 um (pargyline) and 4 mM (CaCl$_2$) separately.

Preparation of radioligand: 50 µl mother liquor is diluted to 5 ml with anhydrous ethanol, and stocked for use.

Preparation of non-labeling ligand: appropriate amounts of 5-HT and Methysergide are dissolved in ultrapure water to give solutions with final concentrations of 2*10$^{-5}$M respectively.

Preparation of solutions of various test drugs: appropriate amount of each drug is first diluted to 1 ml with ultrapure water as stock solution. When needed, 10 µl of the stock solution is diluted to 1 ml to reach a level of 10$^{-5}$M.

Toluene scintillation liquid: PPO (5.0 g) and POPOP (0.1 g) are added in toluene (1000 ml).

2.2 Preparation of Membrane Receptors

Rats are decapitated to get the brains. The target tissues (left and right cerebral cortex) are separated on ice, added with 10-fold volume (V/W) of ice-cold buffer, and homogenized with tissue Homogenizer for several seconds 3 times to form tissue homogenate. The tissue homogenate is centrifuged with low temperature superb centrifuge (12000 r/min) 3 times, with each for 20 minutes. The supernatant is discarded and the precipitate (membrane receptor) is stocked in −80° C. ultralow temperature freezer.

2.3 Competitive Binding Tests of Receptors

The membrane receptor is added with certain volume of ice-cold buffer and homogenized to make membrane receptor solutions at certain concentrations.

Various reaction solutions are added in the following sequences and ratios:

Total binding tube: 100 µl membrane receptor+100 µl buffer+10 µl radioligand

Non-specific tube: 100 µl membrane receptor+100 µl non-labeling ligand+10 µl radioligand Test compound tube: 100 µl membrane receptor+100 µl drug solution+10 µl radioligand Above tubes are put in 37° C. water bath immediately after finishing adding radioligand into each of them and then incubated for 25 min. After 25 min, the tubes are put in ice water to quench the reaction. Each tube is poured into suction filtration device to filter, and the filter membrane is washed with 5-10 ml ice-cold buffer twice. The filter membrane is dried in 85° C. oven, and then put into test tubes, and added with certain amount of scintillation liquid to soak overnight. Radioactivity is determined using liquid scintillation counter.

The percentage inhibition rate for binding of each compound to radioligand is calculated with the following equation: inhibition rate (I %)=(total binding tube cpm−compound cpm)/(total binding tube cpm−non-specific binding tube cpm)×100%

Each compound is tested in duplicate, and the tests are carried out independently twice.

3. Experimental Results

In vitro binding tests of compounds to 5-HT$_{1A}$ and 5-HT$_{2A}$ receptors are seen in Table 1.

TABLE 1

Affinity results of hydrochloride of compound III-1-III-14 to 5-HT$_{1A}$ and 5-HT$_{2A}$ receptors.

| Compound No. | 5-HT$_{1A}$ affinity | | 5-HT$_{2A}$ affinity | |
|---|---|---|---|---|
| | µmol/L | [$^3$H]-8-OH-DPAT | µmol/L | [$^3$H]-Ketanserin |
| aripiprazole | 10 | 118 | 10 | 126 |
| III-1 | 10 | 154.39 | 10 | 98.86 |
| III-2 | 10 | 118.92 | 10 | 130.54 |
| III-3 | 10 | 154.95 | 10 | 106.59 |
| III-4 | 10 | 126.14 | 10 | 103.8 |
| III-5 | 10 | 121.49 | 10 | 133.52 |
| III-6 | 10 | 91.56 | 10 | 84.55 |
| III-7 | 10 | 83.21 | 10 | 101.48 |
| III-8 | 10 | 108.01 | 10 | 111.2 |
| III-9 | 10 | 124.54 | 10 | 153.7 |
| III-10 | 10 | 108.97 | 10 | 144.88 |
| III-11 | 10 | 102.23 | 10 | 144.63 |
| III-12 | 10 | 113.79 | 10 | 132.33 |
| III-13 | 10 | 119.40 | 10 | 148.55 |
| III-14 | 10 | 112.13 | 10 | 135.24 |

2) In Vitro Selective Inhibition Effects of Compounds to Serotonin Reuptake

1. Experimental Materials

Isotope: [$^3$H]-5-HT

GF/C glass fiber filter paper; lipid-soluble scintillation liquid.

Positive control compound: fluoxetine.

2. Experimental Methods

Sample treatment: about 1 mg of compound is weighted and added with relative amount of DMSO to prepare 10$^{-2}$M stock solution. Before use, the stock solution is diluted with HBSS buffer to relative concentrations. Each sample is dissolved in DMSO completely. The dilution is clear and without obvious cloudy and formation of precipitate after adding with buffer.

Experiment system test and positive compound related data test:

(1) Cells which can stably express hSERT are seeded into 24-well plates respectively.

(2) Experiments are started when the cell confluence reaches 80-90%.

(3) Liquids in the plates are discarded, the plates are washed with PBS twice at room temperature.

(4) 160 µl HBSS is added into each well, and then 20 µl positive drug fluoxetine of different concentrations are added (final concentrations are 10$^{-10}$, 10$^{-9}$, 10$^{-8}$, 10$^{-7}$, 10$^{-6}$, 10$^{-5}$ M respectively). 20 µl HBSS (containing 10 µM of pargyline, Vit C and tropolone respectively) is added into the total intake well.

(5) Plates are incubated at 37° C. for 10 min after slight oscillation.

(6) Then 20 µl radioisotope is added (cpm: about 20000).

(7) Plates are incubated at 37° C. for 5 min after slight oscillation.

(8) Liquids in the plates are discarded, the plates are washed with ice-cold PBS twice, all the liquids in the plates are removed away.

(9) NaOH (2M, 100 μl) is added into each well to lyse the cells. All the lysates are combined and put on GF/C glass fiber filter paper.

(10) The filter papers are dried and put in 0.5 ml centrifuge tube, 500 μl lipid soluble scintillation liquid are added. Radioactivity is determined by MicroBeta liquid scintillation counter. Each concentration is tested intriplicate, and tests are carried out independently twice.

Screening of Test Compounds:

Test concentration is 10 μmol/L. The positive drug provided is set as control (10 μmol/L) in each experiment. The experimental processes are the same as the above process.

3. Experimental Results

At the same concentration, inhibition rates of fluoxetine as positive control and test compounds to 5-HT reuptake are listed in Table 2.

TABLE 2

Inhibitory activities of hydrochloride of compounds III-1-III-14 to 5-HT reuptake

| Compound No. | Final concentration μmol/L | Inhibition rates of SERT reuptake [$^3$H]-5-HT |
|---|---|---|
| fluoxetine | 10 | 100% |
| III-1 | 10 | 97.32% |
| III-2 | 10 | 97.82% |
| III-3 | 10 | 98.31% |
| III-4 | 10 | 93.36% |
| III-5 | 10 | 99.70% |
| III-6 | 10 | 98.31% |
| III-7 | 10 | 81.68% |
| III-8 | 10 | 98.31% |
| III-9 | 10 | 103.66% |
| III-10 | 10 | 94.35% |
| III-11 | 10 | 96.63% |
| III-12 | 10 | 94.41% |
| III-13 | 10 | 86.90% |
| III-14 | 10 | 98.21% |

5-HT reuptake concentration gradient experiments are conducted for hydrochloride of compounds III-8 and III-10 to determine their $IC_{50}$, the results are listed in Table 3.

TABLE 3

$IC_{50}$ of hydrochloride of compounds III-8 and III-10 that inhibit 5-HT reuptake

| Compound No. | $IC_{50}$ nM(x ± sd) |
|---|---|
| fluoxetine | 246 |
| III-8 | 246 ± 94 |
| III-10 | 138 ± 35 |

As shown by above experimental results: when the concentration is 10 μmol/L, hydrochloride of compounds III-1-III-14 have high affinity to $5-HT_{1A}$ and $5-HT_{2A}$ receptors; and hydrochloride of compounds III-1-III-14 have high inhibition activities to 5-HT reuptake.

In particular, as shown by results of 5-HT reuptake concentration gradient experiments: hydrochloride of compound III-8 has high inhibition activity to 5-HT reuptake and the inhibition effect is comparable to that of fluoxetine, and the inhibition effect of hydrochloride of compound III-10 to 5-HT reuptake is more potent than that of fluoxetine.

Example 17

Rat formalin induced pain model is used to test in vivo analgesic effect of hydrochloride of compound III-10.

Rat formalin induced pain model is established by Dubuisson and Dennis in 1977. It can simulate some characteristics of human pains after damages, and its persistent tension pain is similar to common clinical chronic pains. Its experimental results have excellent repeatability, and it is considered to be universally accepted pain model which is more reliable than short-term mechanical or thermal stimulation models. It has been generally used in investigation and determination of pain mechanism, pain physiology and pharmacology, screening of the analgesic effects of drugs and evaluation of analgesic drugs.

1. Experimental Materials

Test compounds are prepared to relevant doses with 0.5% CMC-Na before use.

Formaldehyde solution: batch number HN20041109, HuaDong reagent industrial company. In experiment, it is diluted to 5% formaldehyde solution with 0.9% sodium chloride injection.

CMC-Na: provided by Jiangsu EnHua pharmaceutical Co., Ltd.

Sodium chloride injection: batch number H32026305, Fifth pharmaceutical Co., Ltd. XuZhou Stopwatch, counter, homemade observation glass device.

2. Experimental Animals

90 SD rats of weight (240-350 g), half female and half male, are fed for I week to adapt the environment, with 5 in each cage during feeding, the rats are fed under standard condition during experiments with free access to water and food.

3. Experimental Methods

90 SD rats of weight 240-350 g are randomly divided into 9 groups which are negative control group, model group, gabapentin group, high, median and low dosage group of each compound respectively, with 10 rats in each group, half female and half male. Relevant test compounds are given by intragastric administration, and 5% formalin (50 ul) is subcutaneously injected at the left rear foot in 1 h to model, formation of pichu indicates a successful modeling. 0.5% (weight percentage) CMC-Na is given by intragastric administration in negative control group, and normal saline (50 ul) is subcutaneously injected at the bottom of right rear foot in 1 h. After modeling, the leg-raising times in 1-2 minutes and 5-6 minutes are observed. The time period 10-60 minutes are divided into 5 minutes intervals, and the leg-raising times of the first minute of each interval (10-11, 15-16, 20-21, 25-26, 30-31, 35-36, 40-41, 45-46, 50-51, 55-56, 60-61) are observed.

Measuring index is expressed as mean±standard deviation (Mean±SD), comparison is analyzed with One-way ANOVA.

4. Experimental Results

Analgesic activity of hydrochloride of compound III-10 in rat formalin induced pain model is listed in Table 4.

TABLE 4

Effect of hydrochloride of compound III-10 to leg-raising times in rat formalin induced pain model

| compound | dosage (mg/kg) | phase I times(time) | phase II times(time) |
|---|---|---|---|
| Negative group | — | 2.30 ± 4.08** | 2.90 ± 6.10** |
| Model group | — | 29.89 ± 14.65 | 96.22 ± 32.31 |
| Gabapentin group | 100 | 11.60 ± 6.75 | 74.7 ± 39.45 |
| III-10 | 40 | 21.23 ± 11.24 | 42.10 ± 36.39** |
|  | 80 | 16.20 ± 8.05** | 44.90 ± 36.28** |
|  | 160 | 21.90 ± 15.48 | 41.40 ± 38.80** |

(Note:
n = 10, Mean ± SD,
*P < 0.05,
**P < 0.01 VS model group)

In phase I pain, the leg-raising times in group of hydrochloride of III-10 (80 mg/kg) obviously decreased comparing to model group, with statistical significance ($P<0.05$), as shown in Table 4.

Figure 2:
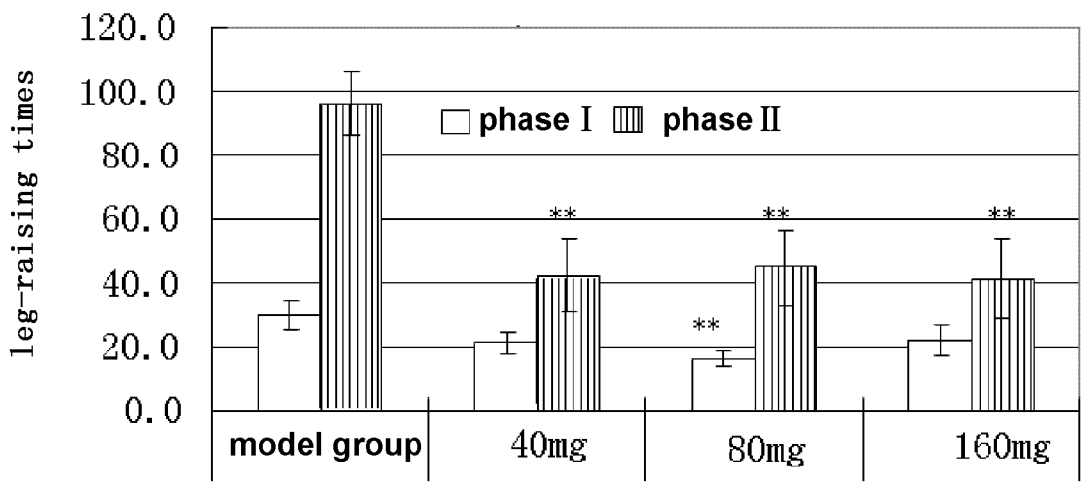
FIG. 2 is effect of hydrochloride of compound III-10 on leg-raising times of rats in formalin model.

In phase II pain, the leg-raising times in group of hydrochloride of III-10 (40 mg/kg, 80 mg/kg, 160 mg/kg) obviously decreased comparing to model group, with statistical significance ($P<0.05$), as shown in Table 4, FIG. 1 and FIG. 2.

FIG. 1 shows effect of positive drug gabapentin to rat leg-raising times in formalin induced pain model (n=10, Mean±SEM), FIG. 2 shows effect of hydrochloride of compound III-10 to rat leg-raising times in formalin induced pain model (n=10, Mean±SEM).

Example 18

In vivo anti-depression effect of hydrochloride of compound III-8 is determined using mice tail suspension test.

1. Experimental Materials 1.2 Main Reagents

Test sample: hydrochloride of compound III-8
Control drug: duloxetine hydrochloride, fluoxetine hydrochloride
CMC-Na: purchased from Shanghai Yuanhong chemical Cor., Ltd.

1.3 Experimental Animals

KM mice, female and male, weight of 20-25 g/each.

2. Experimental Methods

Mice Tail Suspension Test

A few days before the experiment, mice with qualified body weight are selected and divided into groups. The experiments are carried out in 2 days. In D1, mice are put on bar of tail suspension instrument for 6 min, the immobility time of the last 4 min are recorded. Mice with immobility time of 60 s-180 s are selected and set into four levels including 60 s~90 s, 90 s~120 s, 120 s~150 s, 150~180 s, and are randomly divided in each level with 10 mice in each group. Blank control group, positive control group and each test compound group are set.

In D2, mice are put on bar of tail suspension instrument for 6 mins in 1 h post intragastric administration, the immobility time of the last 4 min are recorded (immobility standard: immobility means mice on suspension instrument bar stop struggling or exhibit swinging status).

3. Statistical Methods

The mean values of immobility time for each group are calculated, the results are expressed as "mean±standard deviation". T tests of the results of administration group to control group are conducted to evaluate if the test compound have antidepressive activity, $P<0.05$ is considered significant.

4. Experimental Results

It is observed by experiments that, when compared with blank control group, the groups in which dutoxetine hydrochloride and fluoxetine hydrochloride are given intragastrically at 40 mg/kg have significantly decreased immobility time. In the groups where 20, 40, and 80 mg/kg dosages of hydrochloride of compound III-8 are given intragastrically, there are significant differences comparing with blank control group. The results are listed as follows:

TABLE 5

Rat tail suspension test results of hydrochloride of compound III-8

| group | n | dosage (mg/kg) | Immobility time(S) | Mode of administration |
|---|---|---|---|---|
| Black control group | 10 | — | 108 ± 45.7 | — |
| fluoxetine | 10 | 40 | 69.9 ± 27.4* | Intragastric administration |
| dutoxetine | 10 | 40 | 28.2 ± 27.3** | Intragastric administration |
| III-8 | 10 | 20 | 68.5 ± 33.8* | Intragastric administration |
| III-8 | 10 | 40 | 63.3 ± 30.5* | Intragastric administration |
| III-8 | 10 | 80 | 47.6 ± 31.0** | Intragastric administration |

Note:
*P < 0.05,
**P < 0.01

It is shown by above experiment results: comparing with blank control and positive control, hydrochloride of compound III-8 show notable antidepressive effect when given intragastrically at 20, 40, 80 mg/kg dosages.

Example 19

Acute toxicity study of hydrochloride of compounds III-8 and III-10:

Bliss method is used for statistics. The $LD_{50}$ of single drench of hydrochloride of compound III-8 to mice is 1800 mg/kg; The $LD_{50}$ of single drench of hydrochloride of compound III-10 to mice is 1500 mg/kg.

Example 20

Bacterial reverse mutation test of hydrochloride of compounds III-8 and III-10
Strains: *Salmonella typhimurium* histidine auxotrophic mutants TA97, TA98, TA100 and TA102.

Results: the experiments include two parts of −S9 and +S9. In the test system without S9, TA98 5000 μg/dish has antibacterial activity, and in the test system with S9, TA97 5000 μg/dish has antibacterial activity. Other dosages have no antibacterial activity to any of the strains, and the growth background is excellent. Whether there is S9 or not in the system, all the dosages of compounds III-8 and III-10 do not cause any obvious increase of colony reverse mutations. Ames test is negative.

It is shown by above results: hydrochloride of compound III-10 has high affinity to 5-$HT_{1A}$ receptor and 5-$HT_{2A}$ receptor in in vitro tests, and meanwhile has higher inhibitory effect to 5-HT reuptake; in rat formalin induced pain model, three dosages of hydrochloride of compound III-10 all have obvious anti-neuralgia activity by intragastric administration, and it has good oral absorption; Ames test of hydrochloride of compound III-10 is negative; for single drench of hydrochloride of compound III-10 to mice, the acute toxicity is low and the therapy index is high, and the compound has the potential of development as novel anti-neuralgia drugs.

It is shown by above results: hydrochloride of compound III-8 has high affinity to 5-$HT_{1A}$ receptor and 5-$HT_{2A}$ receptor in in vitro tests, and meanwhile has higher inhibitory effect to 5-HT reuptake; in mice tail suspension test, three dosages of hydrochloride of compound III-8 all have obvious antidepressive effect by intragastric administration, and it has good oral absorption; Ames test of hydrochloride of compound III-8 is negative; hydrochloride of compound III-8 has low acute toxicity and high therapy index, and has the potential of development as novel antidepressive drugs.

What is claimed is:

1. A 3-cyanoanilinoalkylarylpiperazine derivative having a structure according to formula (III), or salt thereof:

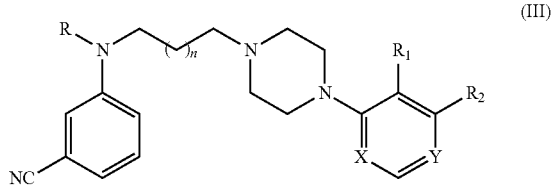

(III)

wherein:
R is $C_1$-$C_5$ linear or branched alkyl, wherein the hydrogen atom(s) of the alkyl may be optionally replaced by 1-3 fluorine atoms;
$R_1$ is H, $OCH_3$, Cl or $CH_3$;
$R_2$ is H, $CF_3$, Cl or $CH_3$;
X and Y are independently CH or N; and
n=0, 1 or 2.

2. The 3-cyanoanilinoalkylarylpiperazine derivative according to claim 1, wherein R is methyl, ethyl, trifluoromethyl, n-propyl or isopropyl.

3. The 3-cyanoanilinoalkylarylpiperazine derivative according to claim 1, wherein:
R is methyl, ethyl, trifluoromethyl, n-propyl or isopropyl;
$R_1$ is H, $OCH_3$, Cl or $CH_3$;
$R_2$ is H, $CF_3$, Cl or $CH_3$;
X and Y are independently CH or N; and
n=0 or 1.

4. The 3-cyanoanilinoalkylarylpiperazine derivative according to claim 1, wherein:
R is methyl, ethyl, trifluoromethyl, n-propyl or isopropyl;
$R_1$ is H, $OCH_3$, Cl or $CH_3$;
$R_2$ is H, $CF_3$, Cl or $CH_3$;
X and Y are independently CH or N; and
n=0.

5. The 3-cyanoanilinoalkylarylpiperazine derivative according to claim 1, wherein:
R is methyl, ethyl, trifluoromethyl, n-propyl or isopropyl;
$R_1$ is H, $OCH_3$, Cl or $CH_3$;
$R_2$ is H, $CF_3$, Cl or $CH_3$;
X and Y are independently CH or N; and
n=1.

6. A 3-cyanoanilinoalkylarylpiperazine derivative selected from:
3-((2-(4-(2-methoxyphenyl)piperazin-1-yl)ethyl)methylamino) benzonitrile,
3-(methyl(2-(4-(3-trifluoromethylphenyl)piperazin-1-yl)ethyl)amino) benzonitrile,
3-((2-(4-(3-chlorophenyl)piperazin-1-yl)ethyl)methylamino) benzonitrile,
3-((2-(4-(2,3-dichlorophenyl)piperazin-1-yl)ethyl)methylamino) benzonitrile,
3-((2-(4-(2,3-dimethylphenyl)piperazin-1-yl)ethyl)methylamino) benzonitrile,
3-((2-(4-(6-chloro-5-methoxylpyrimidin-4-yl)piperazin-1-yl)ethyl)methylamino) benzonitrile,
3-((2-(4-(5-methoxypyrimidin-4-yl)piperazin-1-yl)ethyl)methylamino) benzonitrile,
3-(methyl(3-(4-(3-trifluoromethylphenyl)piperazin-1-yl)propyl)amino) benzonitrile,
3-((3-(4-(2-methoxyphenyl)piperazin-1-yl)propyl)methylamino) benzonitrile,
3-((3-(4-(3-chlorophenyl)piperazin-1-yl)propyl)methylamino) benzonitrile,
3-((3-(4-(2,3-dimethylphenyl)piperazin-1-yl)propyl)methylamino) benzonitrile,
3-((3-(4-(5-methoxylpyrimidin-4-yl)piperazin-1-yl)propyl)methylamino) benzonitrile,
3-((3-(4-(2,3-dichlorophenyl)piperazin-1-yl)propyl)methylamino) benzonitrile, or
3-((3-(4-(2-methoxyphenyl)piperazin-1-yl)propyl)ethylamino) benzonitrile;
or salt thereof.

7. A salt of a 3-cyanoanilinoalkylarylpiperazine derivative according to claim 1, wherein the salt is a hydrochloride, hydrobromide, sulfate, trifluoroacetate or methanesulfonate.

8. The salt of a 3-cyanoanilinoalkylarylpiperazine derivative according to claim 7, wherein the salt contains 0.5-3 molecules of ordered water per molecule of 3-cyanoanilinoalkylarylpiperazine derivative.

9. A pharmaceutical composition, comprising a therapeutically effective amount of a 3-cyanoanilinoalkylarylpiperazine derivative of claim 1 and a pharmaceutically acceptable carrier.

10. A salt of a 3-cyanoanilinoalkylarylpiperazine derivative according to claim 6, wherein the salt is a hydrochloride, hydrobromide, sulfate, trifluoroacetate or methanesulfonate.

11. The salt of a 3-cyanoanilinoalkylarylpiperazine derivative according to claim 10, wherein the salt contains 0.5-3 molecules of ordered water per molecule of 3-cyanoanilinoalkylarylpiperazine derivative.

12. A pharmaceutical composition, comprising a therapeutically effective amount of a 3-cyanoanilinoalkylarylpiperazine derivative of claim 6 and a pharmaceutically acceptable carrier.

13. The 3-cyanoanilinoalkylarylpiperazine derivative according to claim 1, wherein:
R is methyl, or ethyl;
$R_1$ is H, $OCH_3$, Cl or $CH_3$;
$R_2$ is H, $CF_3$, Cl or $CH_3$;

X and Y are independently CH or N; and n=0 or 1.

14. A method of treating pain in a human subject in need thereof, comprising administering a therapeutically effective amount of a 3-cyanoanilinoalkylarylpiperazine derivative of claim 1, or salt thereof, to said human subject.

15. The method of claim 14, wherein the pain to be treated is selected from: nociceptive pain, acute pain, chronic pain, neuropathic pain, and combinations thereof (mixed pain).

16. The method of claim 14, wherein the pain to be treated is selected from: postoperative pain including post cardiosurgery and mastectomy pain, central pain, somatic pain, visceral pain, chronic back pain, neck and waist pain, tumor pain, inflammatory pain, diabetic neuropathic pain, ischialgia, tension headache, cluster headache, daily chronic headache, herpes neuropathic pain, facial and oral neuropathic pain, myofascial pain syndrome, phantom limb pain, amputated limb pain, pain associated with paraplegia, toothache, opioid resistant pain, angina pectoris, pelvic pain, urogenital tract pain including cystitis, vaginal vestibule inflammation and testicular pain, pain associated with early stage menstrual pain syndrome, poststroke pain, pain associated with irritable bowel syndrome, labor pain, postlabor pain, pains induced by burn and chemical injury or sun burn, or bone injury pain.

17. A method of treating pain in a human subject in need thereof, comprising administering a therapeutically effective amount of a 3-cyanoanilinoalkylarylpiperazine derivative of claim 6, or salt thereof, to said human subject.

18. The method of claim 17, wherein the pain to be treated is selected from: nociceptive pain, acute pain, chronic pain, neuropathic pain, and combinations thereof (mixed pain).

19. The method of claim 17, wherein the pain to be treated is selected from: postoperative pain including post cardiosurgery and mastectomy pain, central pain, somatic pain, visceral pain, chronic back pain, neck and waist pain, tumor pain, inflammatory pain, diabetic neuropathic pain, ischialgia, tension headache, cluster headache, daily chronic headache, herpes neuropathic pain, facial and oral neuropathic pain, myofascial pain syndrome, phantom limb pain, amputated limb pain, pain associated with paraplegia, toothache, opioid resistant pain, angina pectoris, pelvic pain, urogenital tract pain including cystitis, vaginal vestibule inflammation and testicular pain, pain associated with early stage menstrual pain syndrome, poststroke pain, pain associated with irritable bowel syndrome, labor pain, postlabor pain, pains induced by burn and chemical injury or sun burn, or bone injury pain.

* * * * *